United States Patent [19]

Wevers et al.

[11] Patent Number: 4,548,757

[45] Date of Patent: Oct. 22, 1985

[54] AQUEOUS AMINOMETHYLENEPHOSPHONIC ACID SOLUTIONS CONTAINING ORGANIC CARBOXYLATE STABILIZING AGENT

[75] Inventors: Jean Wevers, Grimbergen; Hubert Ernst, Brussels; Stephen Cassidy, Tervuren; Christian R. Barrat, Brussels, all of Belgium

[73] Assignee: The Procter & Gamble Company, Cincinnati, Ohio

[21] Appl. No.: 705,573

[22] Filed: Feb. 26, 1985

[30] Foreign Application Priority Data

Mar. 2, 1984 [GB] United Kingdom ................. 8405573

[51] Int. Cl.$^4$ ............................................. C07F 9/38
[52] U.S. Cl. .............................. 260/502.5 E; 252/142
[58] Field of Search ................................. 260/502.5 E

[56] References Cited

U.S. PATENT DOCUMENTS

| | | | |
|---|---|---|---|
| 3,288,846 | 11/1966 | Irani et al. | 260/502.5 E |
| 3,298,956 | 1/1967 | Irani et al. | 260/502.5 E |
| 3,816,333 | 6/1974 | King et al. | 260/502.5 E |
| 3,832,393 | 8/1974 | Krueger et al. | 260/502.5 E |

FOREIGN PATENT DOCUMENTS

| | | | |
|---|---|---|---|
| 766459 | 9/1971 | Belgium | 260/502.5 E |
| 1023785 | 3/1966 | United Kingdom | 260/502.5 E |

*Primary Examiner*—J. E. Evans
*Attorney, Agent, or Firm*—Robert B. Aylor; Richard C. Witte; Thomas H. O'Flaherty

[57] ABSTRACT

Aqueous solutions of aminomethylenephosphonic acid, chiefly diethylenetriaminepenta(methylenephosphonic acid), are disclosed containing a crystallization inhibitor which is an alkali-metal salt of an organic carboxylic acid and residual hydrochloric acid originating from the manufacturing process. The equivalent molar concentration ratio of carboxylic acid salt to hydrochloric acid is greater than 1, preferably from 1.5 to 3.

5 Claims, No Drawings

AQUEOUS AMINOMETHYLENEPHOSPHONIC ACID SOLUTIONS CONTAINING ORGANIC CARBOXYLATE STABILIZING AGENT

This invention relates to aqueous solutions of aminomethylenephosphonic acid, particularly diethylenetriaminepenta(methylenephosphonic acid), having improved stability/homogeneity during prolonged periods of storage. These solutions contain residual hydrochloric acid originating from the manufacturing process. The improvements result from the incorporation of a crystallization inhibitor which is an alkali-metal salt of an organic carboxylic acid with the proviso that the equivalent molar concentration ratio of carboxylic acid salt to hydrochloric acid is greater than 1.

Aminomethylenephosphonic acids such as diethylenetriaminepenta(methylenephosphonic acid) are well-known comodities which have found widespread applications in various domains such as in water treatment and in detergent compositions. In the like application, the phosphonate often functions as crystal growth inhibitor to thus eliminate and/or decrease the earth alkali-metal salt scale formation. In detergent compositions, these phosphonates additionally provide metal sequestration, particularly in relation to transition metals.

Conventional manufacturing processes for aminomethylenephosphonic acid yield concentrated aqueous solutions containing frequently from about 30%–60% of the active phosphonic acid ingredient. Hydrochloric acid, originating from the manufacturing reaction, is present in levels in the range from 2% to 12%, usually from 4% to 10%. The resulting concentrated acid solutions have a tendency to precipitate on storage. The diethylenetriaminepenta(methylenephosphonic acid) component is particularly vulnerable to precipitation behaviour thereby causing shipping and handling inconveniences, particularly with respect to processing control.

The precipitation tendency of certain aminomethylenephosphonic acids had been recognized earlier and remedy has been suggested—see European patent application Ser. No. 0 047 150—particularly by increasing the level of non-oxidizable mineral acid. While the like super-acidified phosphonic acid solutions can be stable during storage, they are excessively corrosive, particularly towards steel and aluminum, i.e., substitute one problem by another.

It is a main object of this invention to provide storage stable aqueous solutions of aminomethylenephosphonic acids containing as the main phosphonate species diethylenetriaminepenta(methylenephosphonic acid).

It is another object of this invention to provide storage stable diethylenetriaminepenta(methylenephosphonic acid) solutions containing a crystallization inhibitor which, in addition to providing storage stability, also is capable of mitigating the pH in a manner to minimize equipment problems, particularly corrosion.

The above and other objects of the invention are now met by incorporating into aqueous aminomethylenephosphonic acid solutions, containing residual hydrochloric acid, a crystallization inhibitor derived from an organo-carboxylic acid.

SUMMARY OF THE INVENTION

It has now been discovered that aqueous storage stable aminomethylenephosphonic acid solutions containing a majority of diethylenetriaminepenta(methylenephosphonic acid) can be obtained by adding to the acid solution of the phosphonic acid component a crystallization inhibitor. The diethylenetriaminepenta(methylenephosphonic acid) solution herein, which also contain residual hydrochloric acid, are stabilized with the aid of a crystallization inhibitor which is an alkali-metal salt of an organic carboxylic acid whereby the equivalent molar concentration ratio of carboxylic acid salt to hydrochloric acid is greater 1, preferably in the range from 1.5 to 3.

The preferred carboxylates can be defined by means of the ratio of the number of carboxylate moieties to the total number of carbon atoms in the organic carboxylic acid salts as being greater than 0.30.

DETAILED DESCRIPTION OF THE INVENTION

The compositions of this invention relate to the stabilization of aqueous solutions of aminomethylene phosphonic acids containing as a major component diethylenetriaminopenta (methylenephosphonic acid). The like compositions are acidic by virtue of residual hydrochloric acid originating from the manufacturing process. The invention resides in the addition of a crystallization inhibitor which is an alkali-metal salt of an organo-carboxylic acid.

The main parameters of the invention herein are explained in more detail below. Unless indicated to the contrary, the "percent" indications stand for "percent by weight".

The claimed technology relates to aqueous solutions of aminomethylenephosphonic acids containing a majority (of the phosphonic acids) of diethylenetriaminepenta(methylenephosphonic acid) (DETPMP). In addition to the pentaphosphonic acid species, industrial material preparations frequently also contain closely-related species having a lower degree of methylphosphonation, such as diethylenetriaminetetra(methylenephosphonic acid) and diethylenetriamine(trimethylenephosphonic acid). The term aminomethylenephosphonic acid used herein is meant to embrace aminomethylenephosphonic acid mixtures with the proviso that at least 50% of the phosphonic acid species are represented by DETPMP. While typical commercial solutions can contain, depending upon intended application, manufacturing technique, etc., from 30 to 60% phosphonic acids, aqueous solutions containing higher or lower levels of aminomethylene phosphonic acids can be prepared.

The aminomethylenephosphonic acid solutions usually contain residual hydrochloric acid originating from the manufacturing process. Frequently, the level of hydrochloric acid, expressed by reference to the total aqueous solution, is in the range from 2% to 12%, more frequently in the range from 4% to 10%.

The crystallization inhibitor is represented by alkali-metal salts of organic carboxylic acids. Non-limiting examples of suitable carboxylic acids include aliphatic carboxylic acids having from 0 to 6 carbon atoms in the alkyl chain such as formic, acetic, and propionic acid; aromatic acids having preferably more than one carboxylic group such as benzene tetracarboxylic acid, mellitic acid; cyclohexane tetra-and hexa-carboxylic acid; aliphatic polycarboxylic acids inclusive of oxalic, succinic, fumaric, maleic acid; hydro-substituted polycarboxylic acids inclusive of: tartaric, citric, itaconic, isocitric and malic acid; and polycarboxylic acids such as polyacrylic, polymethacrylic and polymaleic acid. Copolymeric (poly)carboxylic acids can also be used.)

Preferred carboxylic acid salts herein are those having a ratio of the number of carboxylate moieties to the total number of carbon atoms in the organic carboxylic acid greater than 0.30, preferably from 0.5–1.0. The most preferred organic carboxylic acids are formic, citric, and acetic acid.

The alkali-salt cation can be represented by lithium, potassium and sodium. Most preferred are potassium salts because of their high solubility.

The invention is further defined by the equivalent molar concentration ratio of carboxylic acid salt to hydrochloric acid which shall be greater than 1, preferably from 1.5 to 3. The equivalent molar concentration of the carboxylic acid salts represents the molar concentration (calculated by reference to the salt) multiplied by the number of carboxylate groups in the molecule. The equivalent molar concentration for hydrochloric acid correspond to the molar concentration.

The aminomethylenephosphonic acid solutions in accordance with the invention have a pH, measured at 1% in water at 20° C., above 2.0.

The aqueous phosphonic acid solutions herein are particularly adapted for utilization in detergent compositions, such as liquid heavy duty formulations considering that the stabilizing organic carboxylate salt is capable of exhibiting a specific detergent functionality.

The invention is illustrated by the following examples.

EXAMPLES

A series of aminomethylenephosphonic acid solutions were prepared by adding concentrated aqueous solutions of various carboxylic acid alkali salts to a commercial (aqueous) phosphonate solution containing 50% of aminomethylenephosphonic acid, chiefly diethylenetriaminepenta(methylenephosphonic acid), and 8.2% residual HCl.

The individual solutions were mixed, seeded with crystals of pure diethylenetriaminepenta(methylenephosphonic acid) and stored at room temperature. Effective crystallization inhibition is obtained when the seeds dissolved and gave a clear solution and remained stable for at least one day. The testing results were as follows:

| Example | % Active phosphonic acid content | % Residual Hcl | % Alkali salt of the organic carboxylic acid | Equivalent molar concentration ratio carboxylate: HCl | pH at 1% conc. in distilled water at 20° C. | Solution characteristics after one day |
|---|---|---|---|---|---|---|
| A | 25 | 4.1 | — | — | 1.7 | precipitation |
| B | 25 | 4.1 | 5%; sodium formate | 0.6 | 1.8 | precipitation |
| 1 | 25 | 4.1 | 15%; sodium formate | 2.0 | 2.5 | clear and stable |
| 2 | 25 | 4.1 | 21.5%; potassium acetate | 2.0 | 2.4 | clear and stable |
| 3 | 25 | 4.1 | 22.5; tripotassium citrate | 2.0 | 2.2 | clear and stable |

The above results unequivocally demonstrate the significant benefits derived from the compositions of this invention (Examples 1, 2, 3).

We claim:

1. An aqueous solution of an aminomethylenephosphonic acid, wherein the main phosphonate ingredient is diethylenetriaminepenta(methylenephosphonic acid), containing 2–12% residual hydrochloric acid originating from the manufacturing process, and a crystallization inhibitor which inhibitor is an alkali-metal salt of an organic carboxylic acid, with the proviso that the equivalent molar concentration ratio of carboxylic acid salt to hydrochloric acid is greater than 1.

2. The solution in accordance with claim 1 wherein the ratio of carboxylic salt to hydrochloric acid is from 1.5 to 3.

3. The solution in accordance with claim 1 which is additionally defined in the ratio of the number of carboxylate moieties to total number of carbon atoms in the organic carboxylic acid salt as being greater than 0.30.

4. The solution in accordance with claim 1 wherein the organic carboxylic acid salts are represented by the potassium or sodium salts of formic, citric, or acetic acid.

5. The solution in accordance with claim 4 wherein the ratio of the number of carboxylate moieties to total number of carbon atoms in the organic carboxylic acid salt is in the range from 0.50 to 1.0.

* * * * *